US009326520B2

(12) United States Patent
Pickett et al.

(10) Patent No.: US 9,326,520 B2
(45) Date of Patent: May 3, 2016

(54) PEST REPELLENT COMPRISING GERANYLACETONE

(75) Inventors: John Anthony Pickett, Harpenden (GB); James George Logan, Harpenden (GB); Michael Alexander Birkett, Harpenden (GB); Anne Jennifer Mordue, Aberdeen (GB)

(73) Assignees: The University Court of the University of Aberdeen, Aberdeen (GB); Rothamsted Research Limited, Harpenden (GB)

( * ) Notice: Subject to any disclaimer, the term of this patent is extended or adjusted under 35 U.S.C. 154(b) by 1077 days.

(21) Appl. No.: 12/224,682

(22) PCT Filed: Mar. 2, 2007

(86) PCT No.: PCT/GB2007/000742
§ 371 (c)(1),
(2), (4) Date: Sep. 3, 2008

(87) PCT Pub. No.: WO2007/099347
PCT Pub. Date: Sep. 7, 2007

(65) Prior Publication Data
US 2009/0306217 A1 Dec. 10, 2009

Related U.S. Application Data

(60) Provisional application No. 60/779,109, filed on Mar. 3, 2006.

(51) Int. Cl.
*A01N 49/00* (2006.01)
*A01N 35/02* (2006.01)

(52) U.S. Cl.
CPC ............... *A01N 49/00* (2013.01); *A01N 35/02* (2013.01)

(58) Field of Classification Search
CPC .... A01N 49/00; A01N 35/02; A01N 2300/00
See application file for complete search history.

(56) References Cited

U.S. PATENT DOCUMENTS

| 3,668,226 | A | 6/1972 | Quintana et al. |
| 4,560,551 | A | 12/1985 | Pierce et al. |
| 5,205,065 | A | 4/1993 | Wilson et al. |
| 5,327,675 | A | 7/1994 | Butler et al. |
| 5,738,863 | A | 4/1998 | Sackin et al. |
| 6,203,786 | B1 | 3/2001 | Teale et al. |
| 6,306,415 | B1 * | 10/2001 | Reifenrath ............... 424/406 |
| 6,444,216 | B2 | 9/2002 | Reifenrath |
| 6,660,775 | B2 | 12/2003 | Nolen et al. |
| 2002/0094993 | A1 | 7/2002 | Schnorbach et al. |
| 2003/0138471 | A1 * | 7/2003 | Coats et al. ............... 424/405 |

FOREIGN PATENT DOCUMENTS

| GB | 899289 | 6/1962 |
| GB | 925243 | 5/1963 |
| GB | 945770 | 1/1964 |
| GB | 2388544 A * | 11/2003 |
| GR | 99100213 | 2/2001 |
| JP | 1019004 | 1/1989 |
| JP | 4059702 | 2/1992 |
| JP | 7126110 | 5/1995 |
| JP | 10117657 | 5/1998 |
| JP | 10139602 | 5/1998 |
| JP | 11060421 | 3/1999 |
| JP | 2002308706 | 10/2002 |
| JP | 2002363006 | 12/2002 |
| JP | 2005053813 A * | 3/2005 |
| WO | WO 02/13607 A2 | 2/2002 |
| WO | WO 02/067914 A1 | 9/2002 |
| WO | WO 02/071840 A2 | 9/2002 |
| WO | WO03000431 A1 * | 1/2003 |
| WO | WO 03/009688 A1 | 2/2003 |
| WO | WO 2005/096824 A1 | 10/2005 |

OTHER PUBLICATIONS

Meijerink et. al., J. Insect Physiology, 2001, Pergamon, vol. 47, pp. 455-464.*
Powers et. al., Evolution & Development, 2000, Blackwell, vol. 2, No. 6, pp. 311-325.*
Linn et. al., J. Virology, 2001, Pergamon, vol. 75, issue 9, pp. 4103-4109.*
Hammack et al., Attractiveness of synthetic corn volatiles to feral northern and western corn rootworm beetles (Coleoptera: Chrysomelidae). Environmental Entomology. 1997;26(2):311-317. Retrieved from STN Database Caplus accession No. 1997:337374. Abstract.
Qiu, Sensory and behavioural responses of the malaria mosquito *Anopheles gambiae* to human odours. PhD Thesis, Wageningen University. 2005. 208 pages. Last Accessed on Nov. 19, 2007 from http://library.wur.nl/wda/dissertations/dis3858.pdf>.
Logan et al., "Arm-in-cage testing of natural human-derived mosquito repellents", Malaria Journal 9:239 (2010).

* cited by examiner

*Primary Examiner* — Sarah Pihonak
(74) *Attorney, Agent, or Firm* — VLP Law Group LLP; Richard G. A. Bone (57) ABSTRACT

The present invention provides compositions for inhibiting the activity of an insect pest against a subject (or repelling an insect pest from an environment or preventing attraction to an environment) which compositions comprise geranylacetone as an active ingredient plus a carrier plus a further active ingredient selected from the list consisting of: 6-Methyl-hepten-2-one, octanal, plus optional other chemicals. Also provided are related materials and methods of use.

12 Claims, 7 Drawing Sheets

PEST REPELLENT COMPRISING GERANYLACETONE

This application is a national stage filing under 35 U.S.C. §371 of PCT International application PCT/GB2007/000742, filed Mar. 2, 2007, which claims benefit under 35 U.S.C. §119(e) of the filing date of U.S. provisional application 60/779,109, filed Mar. 3, 2006, the contents of each of which are incorporated herein by reference in their entirety.

TECHNICAL FIELD

The present invention relates generally to methods and materials for use in repelling, or avoiding attracting, biting insects.

BACKGROUND ART

There are numerous publications concerned with the provision of compositions which are said to generally repel or attract (for example to traps) biting insects. These include U.S. Pat. No. 3,668,226; GB 899,289; U.S. Pat. No. 6,444,216; U.S. Pat. No. 6,660,775; WO 03/009688; abstract for JP2002308706; abstract for JP101 17657; abstract for JP10139602; U.S. Pat. No. 4,560,551; WO 02/13607; U.S. Pat. No. 6,203,786; abstract for JP11060421; abstract for JP7126110; GB 925,243; abstract for JP20002363006; abstract for JP1 019004; WO 02/71840; abstract for JP9030906; U.S. Pat. No. 6,660,288.

Interestingly, mosquitoes (Culicidae), midges (Ceratopogonidae) and other flies (Diptera) that bite a range of vertebrate hosts to obtain blood, demonstrate preferences between species and within a host species. However there have been relatively few studies which have investigated inter- and intra-species host-preferences in these organisms [1-9, 14].

Many factors are believed to determine preferences, but for human hosts, studies have demonstrated that differential attraction is determined by volatile olfactory (i.e. volatile chemical) cues that emanate from the skin and associated microorganisms, or breath [15, 16]. Specifically, recent evidence suggests that relative attractiveness is caused by differences in olfactory cues provided by individual hosts [10-13]. However the actual chemical basis for relative attractiveness has remained undefined.

The provision of novel compositions or uses for controlling the behaviour of insects and inhibiting the activity of biting insects against hosts to which they are attracted would provide a contribution to the art.

DISCLOSURE OF THE INVENTION

The present inventors have for the first time demonstrated, counterintuitively, that a repellent, or attractant masking, mechanism is involved in the unattractiveness of individuals to the yellow fever mosquito *Aedes aegypti* and notorious Scottish biting midge, *Culicoides impunctatus*. This is contrary to the assumption in much of the literature that preferences may be dictated by a depleted range of attractants i.e. the view that such 'unattractive' individuals simply did not secrete such attractants.

Briefly, the inventors first established differential attractiveness for the yellow fever mosquito, *Ae. aegypti*, within a group of human volunteers and then collected volatile extracts from their bodies using a novel collection technique. Electrophysiological recordings from the antennae of *Ae. aegypti* and *C. impunctatus*, revealed 23 active compounds, which were identified and quantified. Several chemicals were found to be produced in greater amounts by unattractive individuals and these were further investigated as set out in the Examples below.

The results showed that some of these compounds caused a significant reduction in flight activity of *Ae. aegypti* when presented together with a human hand in the Y-tube olfactometer. A field trial was conducted against *C. impunctatus* and revealed that some of the active compounds were more effectively repellent, at naturally occurring concentrations, than the commercial biting fly repellent DEET. Compounds described herein may thus be used for protection against such insects.

An oral presentation was made at the SOVE (Society of Vector Ecology), 4th International Congress of Vector Ecology, Nugget Hotel/Casino Reno, Nev., Oct. 2-7, 2005 (Thursday, Oct. 6, 2005; Student Paper Session II—Oral Presentations; SP-16 "Laboratory and field experiments on the effects of synthetic odor blends on the behaviour of the malaria mosquito *Anopheles gambiae*" Qui, T. Yu, yu.tongqiu@wur.nl, Wageningen University, Wageningen, The Netherlands, and R. Smallegange, J. Spitzen, J. Cajo, T. Braak, J. Joop, Var Loon, M. Jawara, P. Milligan, B. Knols, W. Takken). The presentation discussed olfactometer and field tests of a number of compounds believed to occur in human fresh and incubated sweat. Certain compounds, including compounds identified by the present inventors below, were shown to be both attractive and repellent in trials.

A thesis (Qiu, Y.T. (2005) "Sensory and behavioural responses of the malaria mosquito *Anopheles gambiae* to human odours". PhD thesis, Wageningen University, The Netherlands) has also published in December 2005.

No comparison of 'attractive' and 'unattractive' individuals was made in these disclosures. No trials based on actual application to host skin were conducted.

Generally the invention provides for methods of controlling the behaviour of insects, the method comprising use of a composition of the invention, as described below, which could for example be applied to a subject or environment.

Thus in one aspect the invention provides a method of inhibiting the activity of an insect pest against a subject, the method comprising applying to a subject a composition of the invention, as described below.

The subject to whom the composition is applied will generally be a species which is a normal host target for the insect pest, and would (in the absence of the composition) otherwise be targeted or attract the insect pest. Subjects to be treated with compounds of the present invention could in principle be human or animal subjects (e.g., dogs, cats, horses, cattle). Preferably the subject is a human subject.

The insect pest is preferably a haematophagous insect e.g. of the family Ceratopogonidae (preferably the genus *Culicoides*), or family Culicidae. Preferably the pest is an insect selected from Table 1.

Most preferably it is a mosquito or midge.

Biting midges belong to the genus *Culicoides* of the family Ceratopogonidae; they are the smallest of the bloodsucking insects and are common pests in the UK, NE United States (where they are called punkies, sand flies, and no-see-ums) and many other places around the world.

The composition will be applied in an amount effective to inhibit the activity of an insect pest against the subject, for example by comparison with the same subject without the composition as determined by standard field methods (such as are used in the Example below; see Ref 18) after any of 1, 5, or 30 minutes.

The examples described below show that compositions of the invention can be used to inhibit attraction towards subjects (for example as demonstrated by significant reduction in upwind flight activity towards the subject). Compositions in the field demonstrated repellency based on a World Health Organisation protocol for testing repellents. Thus it is clear that compositions of the invention can be used to negatively affect host-seeking behaviour by insect pests e.g. reduce the attraction to a subject, or increase the repulsion from the subject, and the terms "inhibition of activity" or "repellent" or the like as used herein will be understood by those skilled in the art accordingly.

Compositions of the invention comprise, or consist essentially of, or consist of, geranylacetone as an active ingredient plus preferably a carrier. The generylacetone will be at a functionally effective amount to inhibit the activity of the insect when in use. Carriers are discussed in more detail hereinafter.

Geranylacetone is alternatively known as 6,10-dimethyl-5,9-undecadien-2-one (cis and trans); 5,9-Undecadien-2-one; 6,10-dimethyl-, trans-Geranylacetone; Nerylacetone; Dihydropseudoionone; 6,10-Dimethyl-undeca-5,9-dien-2-one.

Lwande et al. (1999) Phytochemistry 50: 401-405 analysed the repellency of the essential oil of the anti-tick pasture shrub *Gynandropsis gynandra* in a tick-climbing repellency bioassay. Constituents of the oil were evaluated and included trans-geranylacetone, nononal and many others. It was concluded that the blend of all constituents might act as a general purpose arthropod repellent, although no evidence was offered that this would be effective when actually applied to a host.

The inhibition of activity in the field demonstrated herein for geranylacetone containing compositions is surprising since this has previously been discussed in the context of an attractant for clothes moths (see WO 03/009688) and mites (see abstract for JP2002308706; abstract for JP1 0117657).

In another aspect the compositions of the invention may comprise, or consist essentially of, or consist of, decanal.

The compositions of the invention may comprise, or consist essentially of, or consist of, geranylacetone in combination with one or more other active ingredients defined by the present inventors.

In one embodiment the compositions of the invention may include geranylacetone and 6-methyl-5-hepten-2-one. Such compositions of the invention may also include one or more further compounds selected from the list consisting of: octanal; decanal; nonanal.

6-Methyl-5-hepten-2-one is alternatively known as 6-Methylhept-5-en-2-one; Sulcatone; 5-Hepten-2-one, 6-methyl-; 6-Methyl-5-heptene-2-one; 2-Methyl-2-hepten-6-one; Methyl hept-5-en-2-one; Methylheptenone; 2-Methyl-6-oxo-2-heptene; 2-Oxo-6-methylhept-5-ene.

In one embodiment the compositions of the invention may include geranylacetone and octanal. Such compositions of the invention may also include one or more further compounds selected from the list consisting of: 6-methyl-5-hepten-2-one; decanal; nonanal.

All of the above compounds have shown inhibitory activity in the Examples hereinafter.

Optionally the compositions of the invention also include one or more further compounds selected from the list consisting of: benzaldehyde; naphthalene; acetophenone; (E)-2-octenal).

These compounds have been shown to be present in higher amounts in the skin of 'unattractive' individuals. They may optionally be added to the compositions of the present invention.

The compositions may optionally exclude ingredients such as one or more of: limonene, m-Cymene, 1-alpha-terpineol, beta-cyclocitral, nerol, carvacrol, beta-ionone, nerolidol, and in particular Methyl isothiocyanate. The compositions may exclude ingredients such as one or more of: heptanoic acid, tetradecanoic acid, 3-methyl-1-butanol, 4-ethylpentone.

Thus, in addition to optional further active ingredients, additives, and a carrier as discussed hereinafter, preferred compositions of the present invention comprise geranylacetone in the composition in a concentration of at least about 0.0001% by weight, but may be up to 10, 20, 50, or 99.9% by weight of the total composition.

The carrier may be from 0.1% to 99.9999% by weight of the total composition.

Preferably the compositions of the invention comprise:

| Geranylacetone: | 0.0001-10% |
|---|---|
| more preferably: | 0.001-10% | and optionally one or more further additive compounds selected from the list consisting of:

| 6-Methyl-5-hepten-2-one: | 0.00001-10% |
|---|---|
| Octanal | 0.00001-1% |
| Nonanal | 0.1-10% |
| Decanal | 0.0001-10% | plus optional further active ingredients, additives, and a carrier as discussed hereinafter in order to make 100%. '%' in this context means g/100 g (solid compositions, total weight) or g/100 ml (liquids or ointments, total volume).

Based on the examples set out below, such concentrations of ingredients may be employed for inhibition of flight towards a target.

Based on experiments showing orientation away from the source, compositions of the present invention may in certain embodiments comprise:

| Geranylacetone: | 0.0001-10% |
|---|---|
| and optionally: | |
| Decanal | 0.0001-0.1% |

Compositions of the present invention may comprise:

| Geranylacetone: | 0.001% to 1% |
|---|---| and optionally one or more further compounds selected from the list consisting of:

| 6-Methyl-5-hepten-2-one: | 0.001% and 1% |
|---|---|
| Decanal: | 1% |
| Octanal: | 0.01% |

Examples of such compositions have been shown to be effective against biting midges in field trials.

A preferred mixture for use in the compositions of the present invention will comprise Geranylacetone plus at least one, two, three, four, or five of the preferred additive compounds described above.

A preferred mixture for use in the compositions of the present invention is as follows:

Geranylacetone: 0.00001-10%, more preferably 0.001-10%, more preferably 0.01-10%, more preferably 0.1-5%, most preferably about 1%, and.
6-Methyl-5-hepten-2-one: 0.1-10%, more preferably 0.1-5%, most preferably about 1%.

Another preferred mixture for use in the compositions of the present invention is as follows:
Geranylacetone: 0.00001-10%, more preferably 0.001-10%, more preferably 0.01-10%, more preferably 0.1-5%, most preferably about 1%.
6-Methyl-5-hepten-2-one: 0.1-10%, more preferably 0.5-5%, most preferably about 1%.
Octanal: 0.001-0.1%, more preferably 0.005-0.05%, most preferably about 0.01%.

Based on analysis of 'attractive' and 'unattractive' individuals, for compositions comprising 6-Methyl-5-hepten-2-one and Geranylacetone it is preferred that these are in a weight ratio of at least or equal to about 0.5:1, more preferably at least or equal to about 1:1; 1.5:1; 2:1; 20:1; 200:1 or more.

Other preferred mixtures are discussed in the Examples hereinafter.

Compositions of the present invention may be formulated as ointments or solutions which contain the active ingredients disclosed herein.

The invention further provides use of geranylacetone, preferably in the form of any composition of the invention (as described herein), in the preparation of an inhibitory formulation for treatment of a subject for inhibiting the activity of an insect pest against the subject.

Preferably the composition is for topical application to the subject. For topical application, the formulation may take the form of a spray formulation or a cream or lotion formulation.

Thus the compositions of the present invention may be employed with such solid and/or liquid dispersible carrier vehicles as described herein or as otherwise known in the art, and/or with other known compatible active agents, if desired, in the form of particular dosage preparations for specific application made therefrom, such as solutions, emulsions, suspensions, powders, pastes, and granules as described herein or as otherwise known in the art which are thus ready for use. The formulation may include antioxidants and UV absorbers.

Liquid formulations may be aqueous-based or non-aqueous (i.e., organic solvents such as ethanol as used in the Examples below), or combinations thereof, and may be employed as foams, gels, suspensions, emulsions, microemulsions or emulsifiable concentrates or the like. The ingredients may include Theological agents, surfactants, emulsifiers, dispersants or polymers.

U.S. Pat. No. 6,444,216 discusses the use of volatile silicon fluids to impart mildness and water repellency to insect repellent compositions. As noted therein volatile silicon fluids are available commercially. For example it is reported that Dow Corning uses commercial designations of 244, 245, 246, 344 and 345, which are mixtures of polydimethylcyclosiloxanes (cyclomethicones) and are composed of tetramers (e.g. cyclotetrasiloxane, octamethylcyclotetrasiloxane), pentamers (e.g. cyclopentasiloxane, decamethylcyclopentasiloxane), and hexamers (e.g. cyclohexasiloxane, dodecamethylcyclohexasiloxane). Mixtures of the various silicone fluids, either with other silicone fluids or non-silicon containing substances, are used in a variety of cosmetic preparations to impart special properties, to include water repellency and skin protection.

The formulations may be a solid mixture which releases a vapour having the same composition of active ingredient or ingredients as the solid mixture. Agents to promote sublimation of active ingredients to achieve this are described in GB 925,243.

Thus the present invention also provides a topical formulation for inhibiting the activity of an insect pest against a subject, which formulation consists essentially of a composition of the present invention as described above.

The present invention also provides a topical formulation for inhibiting the activity of an insect pest against a subject, which formulation comprises:
(i) a dermatologically acceptable carrier; and
(ii) a composition of the present invention as described above,
(iii) optionally one or more active ingredients, The present invention also provides an article of manufacture comprising:
(i) a topical formulation for inhibiting the activity of an insect pest against a subject as described above,
(ii) aerosol or other spay means for administering the formulation topically.

Insect repellent compositions are available commercially in aerosol form and aerosol technologies are well known in the art. Consumers find aerosol compositions easy to administer to both the skin and to clothing. Further, aerosol compositions help consumers avoid the inconvenience of having to apply and spread the insect repellent with the hands. U.S. Pat. No. 6,969,521 relates to cosmetically-acceptable aerosol vehicles to disperse and deliver the insect repellent active, the vehicle having a volatile organic compound component.

The present invention also provides an article of manufacture comprising:
(i) a topical formulation for inhibiting the activity of an insect pest against a subject as described above,
(ii) instructions for use of the formulation against the insect pest.

When using the formulations of the present invention, subjects may be directly or indirectly treated, such as by applying the formulation to the skin of the subject, or by applying the formulation to an article worn by or otherwise protecting the subject. For example garments, belts, collars, or other articles worn by the subject from whom insects are to be repelled. Preferred examples may include a slow-release badge worn on clothing; arm, wrist or ankle bands; accessories including pendants, necklaces, bracelets.

The formulation may be applied to netting or screening that protects a subject, particularly a sleeping subject.

In another alternative, the compositions of the invention may be formulated in paints with a conventional microencapsulation technology.

The repellent compounds are suitably applied by any method known in the art including, for example, spraying, pouring, dipping, in the form of concentrated liquids, solutions, suspensions, sprays, powders, pellets, briquettes, bricks and the like, formulated to deliver a repellent effective concentration of the repellent compound. It will be recognized that the concentration, applied amount and frequency of application will vary with the subject and locus of application, e.g., to the skin or hair of a human.

The invention provides for applying the insect repellent formulation to achieve a topical dose of any given active ingredient of between about 0.0025 $\mu g/cm^2$ to 100 $\mu g/cm^2$, more preferably 0.25 $\mu g/cm^2$ to 25 $\mu g/cm^2$. One preferred final concentration is around 10 $\mu g/cm^2$. Based on the application of around 1 ml to a forearm of approximately 400 $cm^2$, this can be achieved by a concentration of around:
0.0001%=0.0025 $\mu g/cm^2$
0.01%=0.25 $\mu g/cm^2$
1%=25 $\mu g/cm^2$
4%=100 $\mu g/cm^2$ As noted above, when using the formulations of the present invention, subjects may not be directly treated. Thus the compositions may be used or applied to an environment (e.g. a pre-defined region, which may or may not be contained) from which it is desired to repel pests (or mask the attractiveness of the environment to pests). Thus as noted above the formulation may be applied to netting or screening that protects a subject. Alternatively it may be provided direct to an environment e.g. by spraying or by use of compositions of apparatus adapted to deliver a repellent effective concentration of the repellent compound.

Thus it will be understood the invention provides a method of repelling an insect pest from an environment or preventing attraction to an environment (e.g. by masking the attractiveness if a subject therein), the method comprising applying to the environment a composition of the present invention e.g. comprising geranylacetone as an active ingredient plus a carrier plus optionally a further active ingredient selected from the list consisting of: 6-methyl-5-hepten-2-one, octanal; decanal; nonanal. The compositions may be any of those discussed above or below.

Application (or dispensing) to an environment may be achieved by conventional means which include (by way of example only): candles, coils, slow release dispensers, (e.g. electric and non-electric vaporisers), electric and non-electric oil burners, electric 'plug-in' diffusers. Numerous such dispensers for volatile substances are very well known to those skilled in the art e.g. for dispensing incense, perfume, medicaments, insecticides, insect repellents, disinfectants, or fumigants. In such dispensers the volatile substance may be formulated as a gel for slow release e.g. with a gelling agent selected from the group consisting of dibenzyllidene sorbital acetal, gellan gum and polyacrylic acid polymers. Any such known dispenser or formulation may be applied analogously in the present invention.

Any such dispenser, comprising (and adapted to dispense) a composition of the present invention (optionally in the form of a gel) provides a further aspect of the present invention, as does a method of dispensing a composition of the present invention comprising use of any such dispenser.

Figure 4:
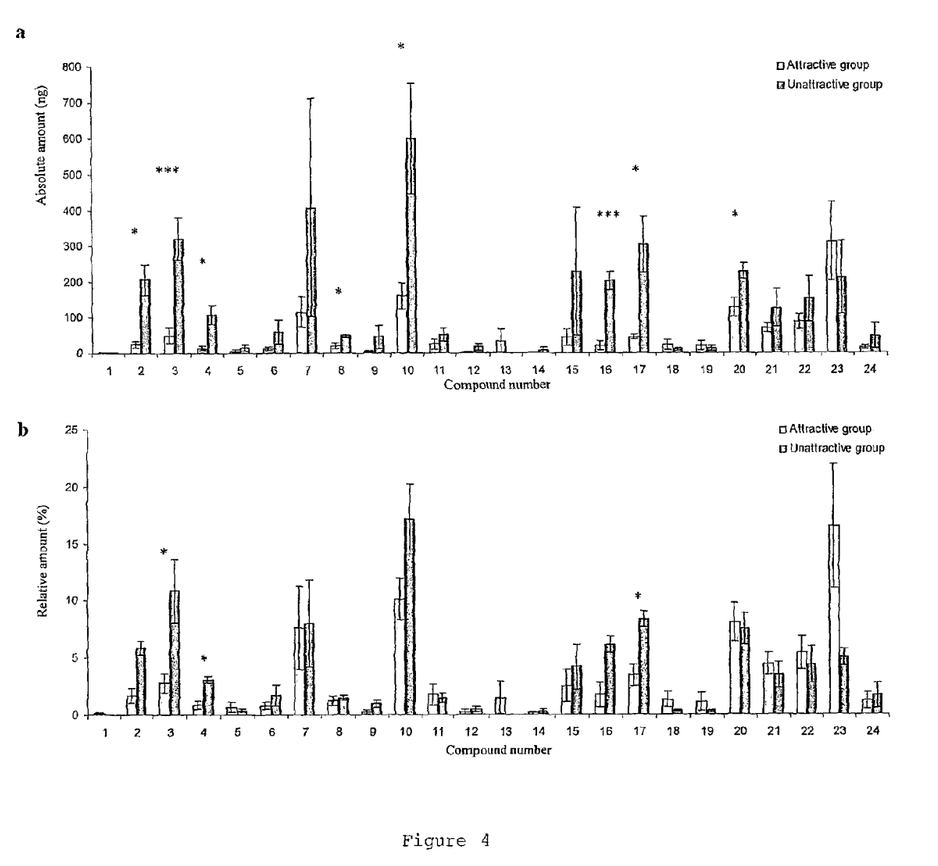

One preferred dispenser is an electrostatic chemical dispenser such as is available from Aerstream Technology Limited (Wallingford, UK). In such a system droplets are electrostatically charged such that they may pervade an environment longer than aerosols. One such system is described in International Patent Application WO03/000431.

Thus an electrostatic chemical dispenser according to the present invention may comprise a) a conduit that contains, in use, liquid to be atomised, which liquid comprises, consists or consists essentially of a composition of the present invention;

b) a spray electrode; and, c) a discharge electrode.

Briefly, in such a system, each electrode is adjacent to a dielectric, wherein the electrodes are connected in an electrical circuit to enable a potential difference to be applied between the spray electrode and the discharge electrode to atomise the liquid and to generate charge carriers of a first polarity in the proximity of the spray electrode and ions of a second polarity in the proximity of the discharge electrode, and wherein some of the first polarity charge carriers deposit on the dielectric adjacent to the spray electrode and some of the second polarity ions deposit on the dielectric adjacent to the discharge electrode so that the atomised liquid is repelled from the dielectric adjacent to the spray electrode and electrically discharged by second polarity ions that are repelled by the dielectric adjacent to the discharge electrode.

It will be understood that any of the active ingredients of the compositions of the present invention may be provided in precursor form. A precursor molecule in this context is one which, during or following application to the skin, is converted to the relevant chemical constituent. Precursors of the compounds specified herein may be readily provided by those skilled in the art based on well established principles—for example compounds containing an olefinic double bond which on oxidation yield the ketone or aldehyde group for these compounds could be utilised. For the ketones, precursors could be squalene or a lower molecular isoprenoid with the appropriate structural requirements and for the aldehydes an unsaturated carboxylic acid with the double bond at ω8, ω9, ω10 could be used.

Precursor molecules may be desired to manipulate properties such as stability, skin retention (i.e. rate of release) and so on. So called “dermal anchoring” molecules are discussed for example in U.S. Pat. No. 3,668,226.

The disclosure herein applies *mutatis mutandis* to the use of such precursor molecules as it does to geranylacetone; 6-methyl-5-hepten-2-one; octanal; nonanal; decanal.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

FIG. 1. Behavioural responses *Aedes aegypti* host-seeking female mosquitoes to the hands of volunteers. a) Flight activity—the proportion of mosquitoes that were recorded upwind in the Y-tube; b) Relative attraction—the proportion of mosquitoes that were recorded in the ‘test’ arm of the Y-tube. Data are presented as differences between the response to the volunteer and the response to the standard stimulus (hand of volunteer Y01). Back transformed means±s.e.d. are shown. Asterisks indicate statistically significant differences from the standard (Y01) (GLM, *$p<0.05$,  $p<0.01$, * $p<0.001$; ns not significant; n=10-12).

FIG. 2. Behavioural responses *Aedes aegypti* host-seeking female mosquitoes to extracts (+$CO_2$) collected from seven volunteers and the standard volunteer (Y01). a) Flight activity—the proportion of mosquitoes that were recorded upwind in the Y-tube; b) Relative attraction—the proportion of mosquitoes that were recorded in the ‘test’ arm of the Y-tube. Back transformed means±confidence intervals (95%) are shown. Asterisks indicate statistically significant differences from the control (GLM, *$p<0.05$,  $p<0.01$, * $p<0.001$; ns not significant; n=10-12).

FIG. 3. Typical coupled GC-EAG traces a). *Aedes aegypti* female mosquito response to human (Y01, attractive) air entrainment extract and *C. impunctatus* midge responses to human (Y05, unattractive) air entrainment extract. Top trace corresponds to the FID detector on the GC. Bottom trace corresponds to the antennal response of the insect preparation. A. benzaldehyde B. 6-methyl-5-hepten-2-one, C. octanal, D. unknown 7, E. nonanal & linalool, F. menthol & naphthalene, G. decanal, H. geranylacetone.

FIG. 4. (a) Absolute total (ng), and (b) mean amounts (%) of EAG active compounds collected from whole body air entrainments of volunteers within the attractive group (n=6) and unattractive group (n=4). Significant differences between the two means are denoted by: *p<0.05;  p<0.01, * p<0.001. Compound numbers: 1. hexanal, 2. benzaldehyde, 3. 6-methyl-5-hepten-2-one, 4. octanal, 5. 1,4-dichlorobenzene, 6. 2-ethylhexanol, 7. limonene, 8. unknown 7, 9. dihydromyrcenol, 10. nonanal, 11. linalool, 12. undecane, 13. (E)-2-nonenal, 14. octanoic acid, 15. menthol, 16. naphthalene, 17. decanal, 18. indole, 19. dodecanal, 20. geranylacetone, 21. pentadecane, 22. hexadecane, 23. α-isomethylionone, 24. heptadecene. Significant differences between the two groups are denoted by *p<0.05,  p<0.01, * p<0.001.

Figure 4C:
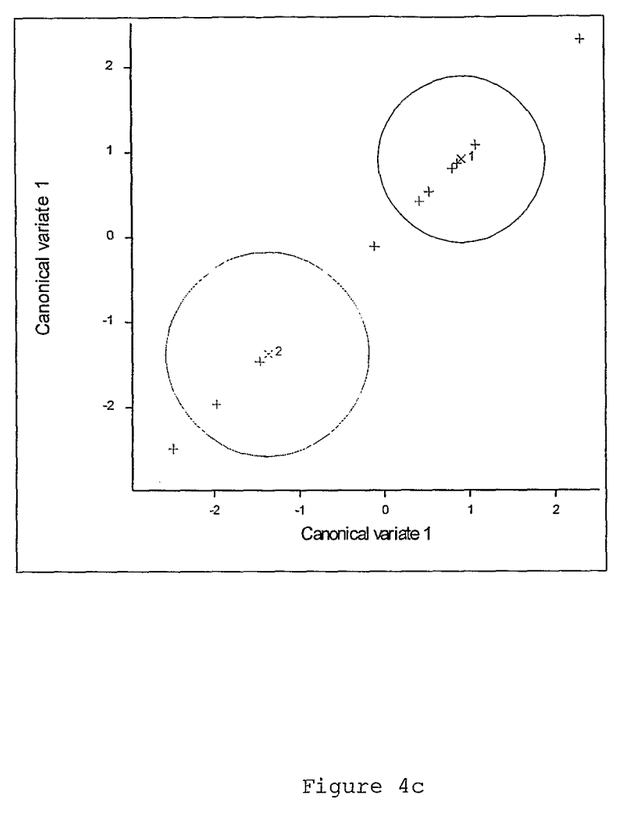

(c) Plot of canonical-variate scores based on the amounts of all GC-EAG active chemicals within air entrainment extracts for all volunteers. Black crosses=Group 1 (attractive individuals); Red crosses=Group 2 (unattractive individuals). Circles represent 95% confidence intervals.

Figure 5:
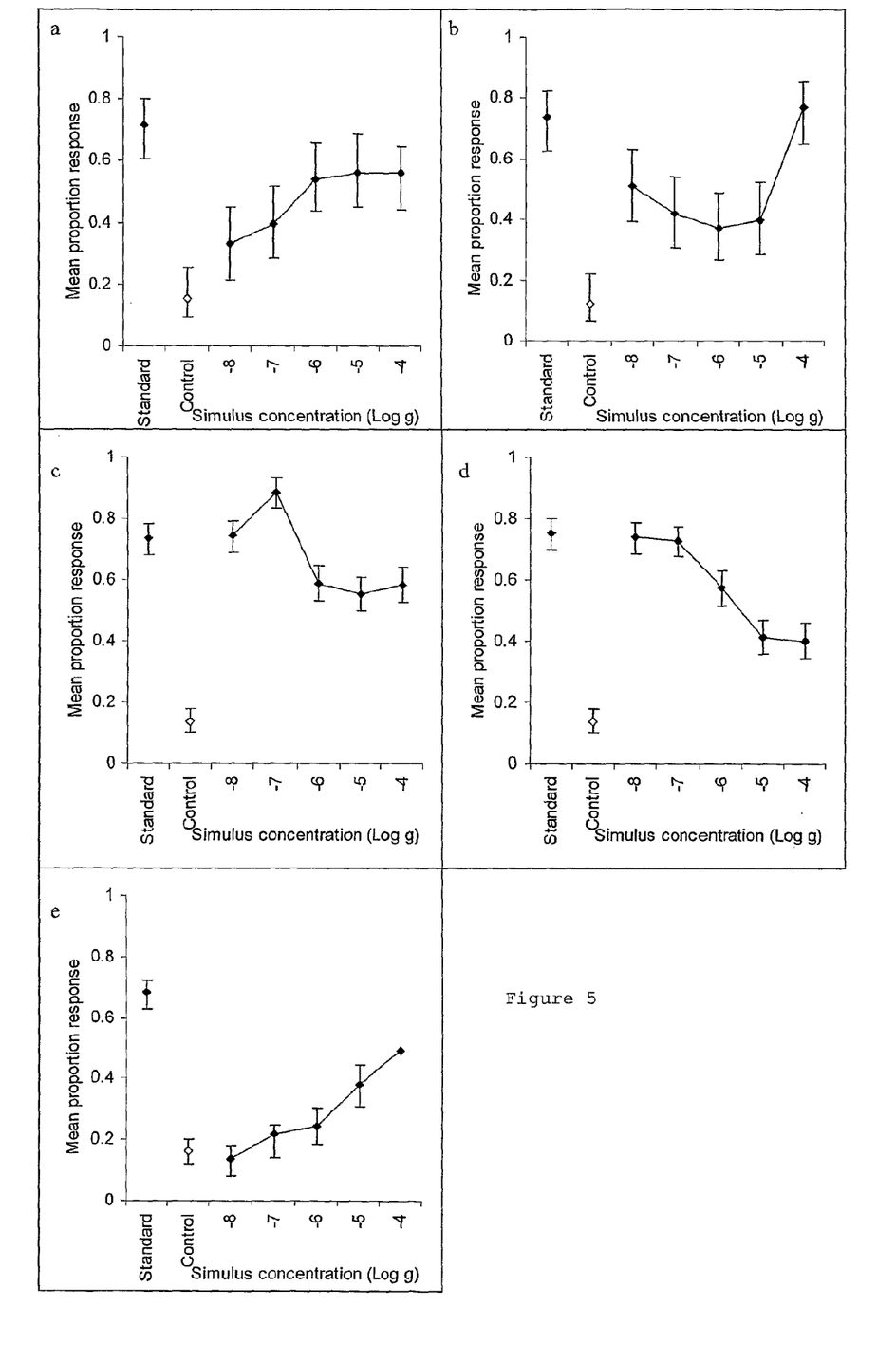

FIG. 5. Mean proportion of *Aedes aegypti* female mosquitoes showing flight activity in the Y-tube in response to the standard (hand of Y01 in one side of the Y-tube and filter paper control in the other) and seven doses of a) 6-methyl-5-hepten-2-one, b) octanal, c) nonanal, d) decanal and e) geranylacetone chemical treatments (hand of Y01+chemical in one side of the Y-tube and filter paper solvent control in the other). ($-1=1\times10^{-1}$ g $\mu L^{-1}$; $-2=1\times10^{-2}$ g $\mu L^{-1}$, etc). Back transformed means+95% confidence intervals (calculated for a binomial distribution) from the logistic scale are shown.

Figure 6:
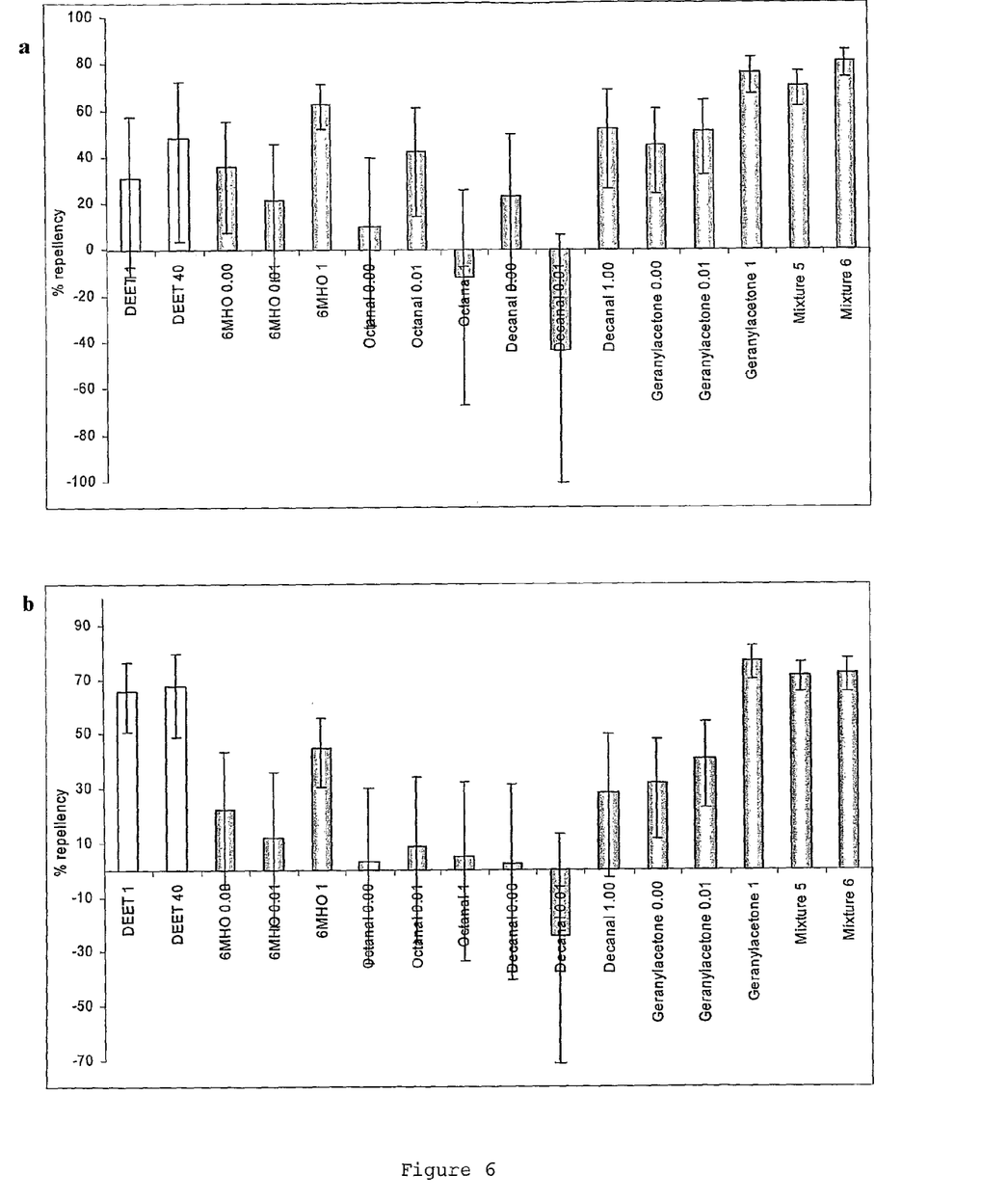

FIG. 6. Repellency of EAG-active human-derived compounds applied to the forearms of volunteers and tested on *Culicoides impuctatus* midges in the field. a) over 1 minute and b) over 5 minutes.

EXAMPLES

Example 1

Defining Attractive and Unattractive Volunteers

Figure 1:
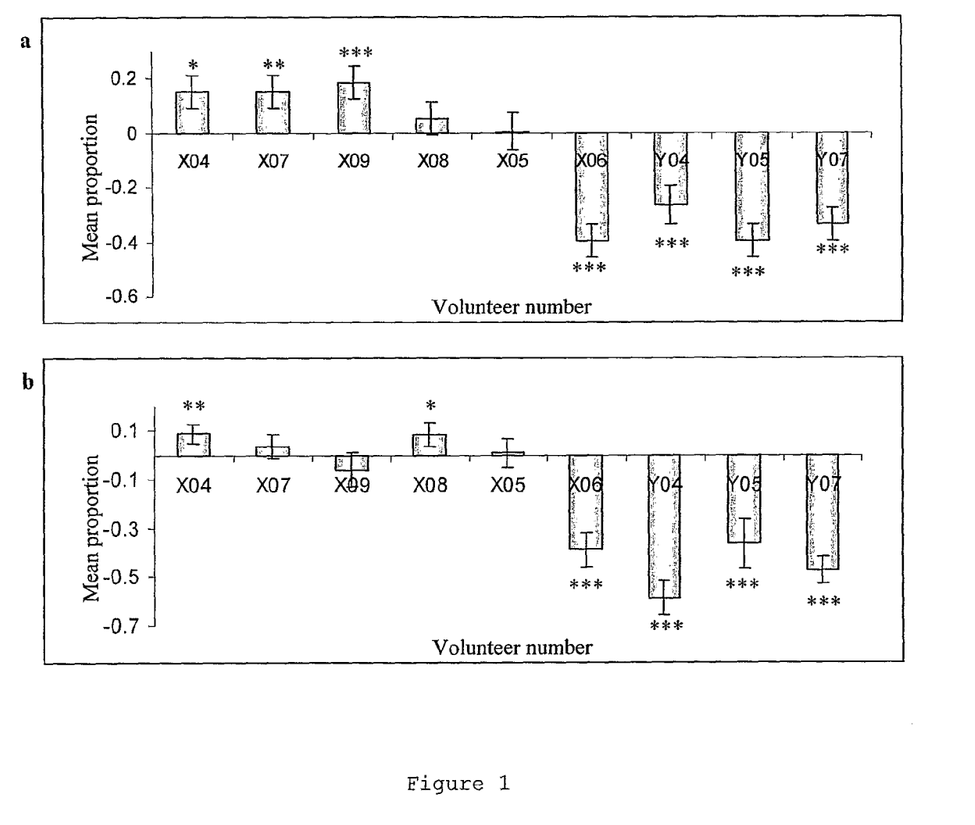

A convenient bioassay was established following work by Geier et al. (1999)[17] using a Y-tube olfactometer in which mosquitoes, *Ae. aegypti*, could "choose" between volatile skin emanations and air alone, the "choice" being expressed as flight activity or relative attraction. Initially, the source of skin emanations was from individual hands of a series of human volunteers. Volunteers were analysed in this way until a range of attractive and unattractive examples were obtained (FIG. 1). Five volunteers (X04, X07, X09, X08 and X05) induced greater upwind flight activity and relative attraction than the standard volunteer (Y01). Four volunteers (X06, Y04, Y05 and Y07) induced significantly less upwind flight activity and relative attraction than the standard (Y01).

Example 2

Obtaining Volatile Chemicals from Volunteers

A novel system was devised for obtaining volatile chemicals from whole bodies. This involved placing each volunteer (and the standard (Y01)) from the attractive and unattractive groups in an aluminiumised plastic bag (Lifesystems™), with the head outside, under positive pressure from clean air and withdrawing air that had passed over the body, to be entrained through a small column of absorbent polymer. This provided samples, the same batch of which could be used for multiple behavioural, electrophysiological and chemical analysis.

Example 3

Confirmation of Validity of Volatile Chemicals from Volunteers

Figure 2:
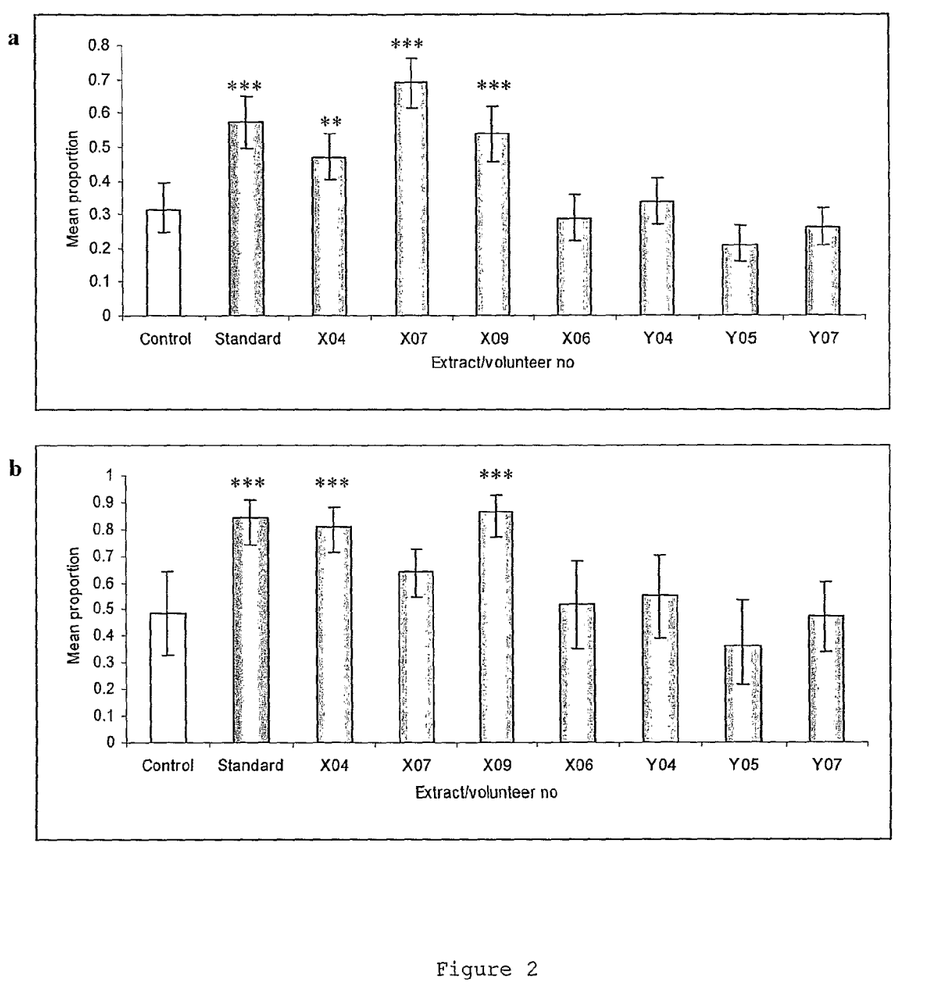

The volatiles were extracted from the polymer and assayed again using the Y-tube olfactometer against an air control and standard volunteer (Y01), all with added $CO_2$ (FIG. 2). For the first time, volatile extracts of human volunteers were shown to exhibit similar attractiveness or unattractiveness to the direct human skin emanations, with extracts from the standard (Y01), X04, X07 and X09 being significantly attractive, and those from X06, Y04, Y05 and Y07 as unattractive as the air control.

Example 4

Comparison and Analysis of Volatile Extracts

Figure 3:
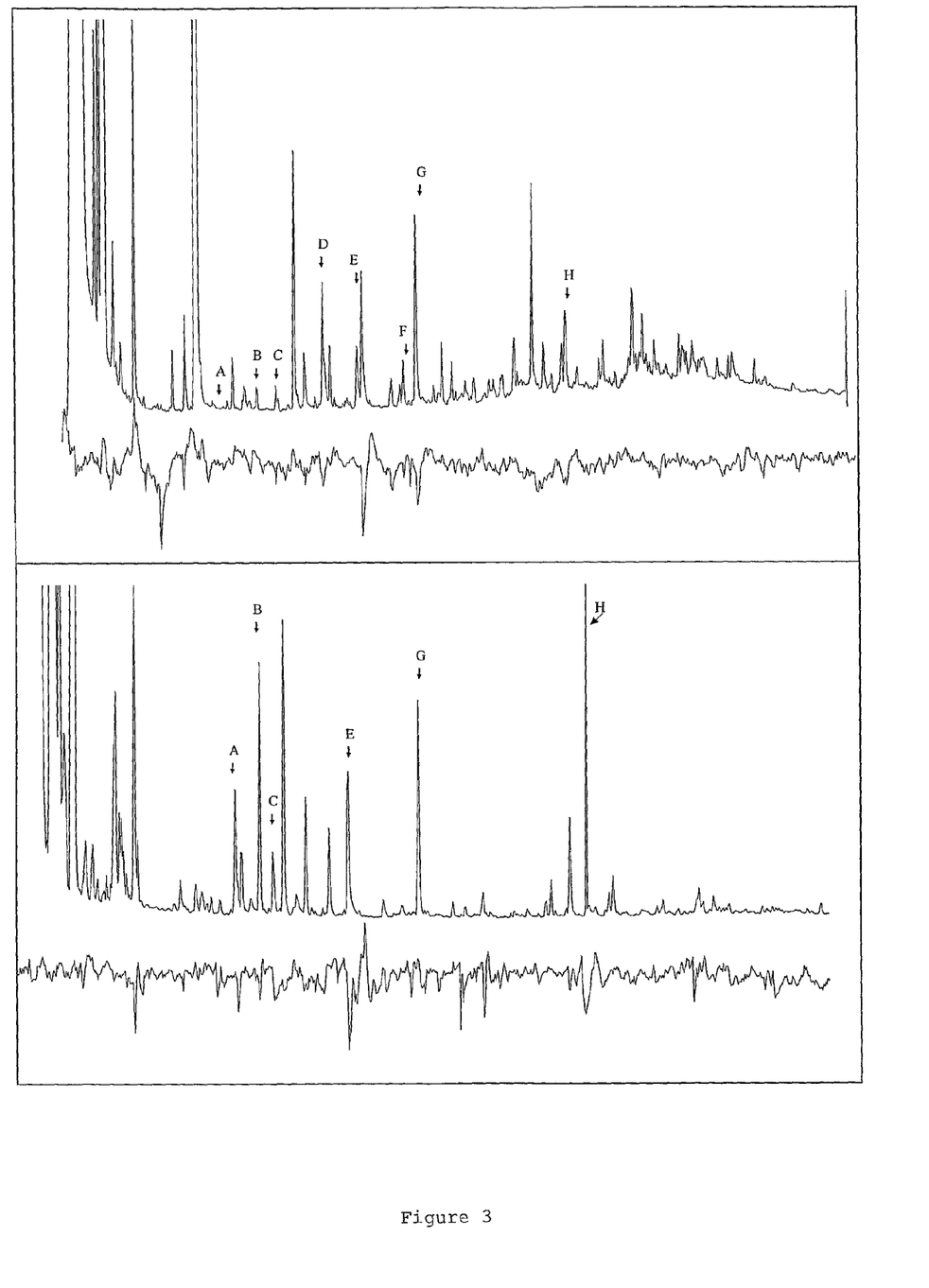

The volatile extracts of the volunteers used in FIG. 2 were then by high resolution GC directly coupled whole antennal electrophysiological preparations, from female *Ae. aegypti*, (6-12 days old) to produce GC-electronantennograms (GC-EAG), typically as shown in FIG. 3. Thus, components which were physiologically active, and therefore likely to be responsible for the differences in attractiveness of the human volunteers, were determined.

Compounds giving the peaks associated with electrophysiological activity by GC-EAG were tentatively identified by GC-MS under similar conditions and the identity confirmed by peak enhancement on GC using two columns of different polarity by coinjection with authentic compounds.

Identifications are listed in Table 2 and absolute amounts, determined by a multiple point external standard method, given. Statistically significant differences between the attractive (Group 1) and unattractive (Group 2) were observed for:
benzaldehyde,
6-methyl-5-hepten-2-one,
octanal,
nonanal,
decanal,
naphthalene
geranylacetone
with the levels being higher, in Group 2.

Additionally the relative amounts (in respect of total chemical composition; see FIG. 4) of 6-methyl-5-hepten-2-one, octanal and decanal were higher.

A number of electrophysiologically active compounds from the 32 active peaks have not been conclusively identified, but only one was believed to be associated with unattractiveness.

unknown 7 (believed to be acetophenone or (E)-2-octenal).

Although a number of electrophysiologically active compounds were chiral the isomeric composition was not determined as these compounds were not implicated as factors contributing to human unattractiveness. Care was made to remove contamination of volunteers, for example with industrial or cosmetic chemicals (see Methods). Nevertheless compounds with electrophysiological activity were shown even if, as with dichlorobenzene and naphthalene, these could have arisen from synthetic sources.

Confirming the grouping of the volunteers, multivariate analysis revealed that the attractive (Group 1) and unattractive (Group 2) groups differed significantly in terms of the variability in the amounts of the seven specified EAG-active chemicals between the two groups (FIG. 4; Table 1).

Tables 3a and 3b show ratio of these compounds from "attractive" volunteers and "unattractive" volunteers.

Example 5

Testing of Candidate Compounds

Based on the results above, five chemicals were chosen as those most likely to be naturally involved in human unattractiveness and were subjected to further analysis:
(i) 6-methyl-5-hepten-2-one,
(ii) octanal,
(iii) nonanal,
(iv) decanal,
(v) geranylacetone These compounds (from Sigma Aldrich) were tested individually at different concentrations in the olfactometer against *Ae. aegypti*. The upwind flight activity, relative attraction and probing activity (feeding) of the mosquitoes to the hand of an attractive volunteer with and without the chemicals was recorded. All chemicals caused a significant reduction in flight activity and geranylacetone caused a reduction in relative attraction (FIG. 5; data for relative attraction not shown). Probing activity (feeding) was also significantly reduced by 6-methyl-5-hepten-2-one and geranylacetone (data not shown).

Thus, it is clear that each of these five demonstrated the ability to interfere significantly with the attractiveness of skin emanations from the hand of an attractive standard volunteer, i.e. Y01, at naturally occurring levels. Only nonanal allowed significantly greater flight activity than the untreated hand but at only one dose.

Only octanal has been described previously as a repellent for *Ae. aegypti* (H. D. Douglas et al. "Chemical Odorant of Colonial Seabird Repels Mosquitoes" *J. Med. Entomol.* 42(4): 647-651 (2005)), and the compounds newly identified here as repellents could be used in defence against these other biting flies and possibly other haematophagous arthropods. The chemical factors conferring low human attractiveness to mosquitoes and midges determined here could be still more effective given a more persistent formulation.

Interestingly, the variation between DEET and a more recent repellent, picaridine (Bayrepel®), shows variability of repellency with human subjects[19]. This may arise in part from the type of individual variation described herein.

Example 6

Further Analysis of Volatile Extracts

The extracts of volunteer human volatiles were also analysed by GC-EAG on *C. impunctatus*, which it is understood is the first time such an investigation had been done with a Ceratopogonid. A typical trace is given in FIG. 3 and the same range of compounds was responded to, but particularly those implicated as giving negative responses in samples from the unattractive volunteers.

Example 7

Field Trials of Compounds

A field trial was made in the Ormsary estate, Argyllshire, during the summer 2005 in a region with an extremely high natural population of *C. impunctatus*. Active compounds at reducing normal human attractiveness to *Ae. aegypti* in the Y-tube olfactometer (6-methyl-5-hepten-2-one; geranylacetone) plus six mixtures, were tested for repellency (Table 4) using a WHO protocol[18]. Compounds were applied to (nylon) stockings and worn on the forearms of volunteers and were tested at three concentrations in ethanol (1%, 0.01% and 0.0001%). All compounds and mixtures were compared against the WHO approved repellent diethyltoluamide (DEET) (1% and 40%).

Results (FIG. 6) show that DEET at 40% was not more repellent than DEET at 1%. Therefore, statistical comparisons were subsequently made between the compounds or mixtures and DEET at 1%.

Individual Compounds

Geranylacetone was effective at all concentrations tested and with a typical dose response of increasing efficacy with increasing concentration.

For 6-methyl-5-hepten-2-one at the 1 min time, at 0.001% is significantly repellent; 0.01% is not repellent but 1% is strongly repellent, indeed more effective than DEET, but was repellent only at 1% over 5 min.

Over 1 min, 1% geranylacetone, 1% 6-methyl-5-hepten-2-one, Mix 5 and Mix 6 were significantly greater than DEET at 1%, and for the full 5 min testing period.

1% geranylacetone, Mix 6 and Mix 5 showed higher % repellency than DEET; these differences were not significant.

Example 8

Additional Field Trials

Methods

Human-derived compounds (6-methyl-5-hepten-2-one and geranylacetone) were tested for repellency against *Anopheles gambiae* and *Culex quinquefasciatus* mosquitoes in laboratory-based repellency tests using an established protocol (Omolo et al., 2004). The mosquitoes were laboratory-reared using standard conditions at ICIPE, Duduville. 5-7 day old female mosquitoes that had been starved for 18 h but previously fed on 6% glucose solution were used. Eighteen cages (50×50×50 cm) were used with 25 female mosquitoes in each. Six human volunteers with no or little allergic reaction to bites were selected. Test solutions (0.5 ml in acetone) were applied to a volunteer's forearms and the hand was covered with a glove. Acetone alone (0.5 ml) served as a control on the other arm. The control arm was inserted into a cage and the number of landings were recorded over 3 min. The treated arm was then inserted as above. Repellency data was expressed as protective efficacy (PE) and was calculated by using the formula PE=(% control mean−% test mean/% control mean). The data were transformed and subjected to an ANOVA.

Each compound was tested at concentrations ranging from 0.0001% to 10%.

Three mixtures were also tested at the same concentrations and comprised the following components:
Mixture 1: 1:1:1:1:1 of 6-methyl-5-hepten-2-one, octanal, nonanal, decanal and geranylacetone
Mixture 2: 1:3:1:0.5:0.5 of 6-methyl-5-hepten-2-one, octanal, nonanal, decanal and geranylacetone
Mixture 3: 1:1 of 6-methyl-5-hepten-2-one and geranylacetone.

Mixture 1 and mixture 3 were then incorporated into a formulation which consisted of emulsifying wax NF, Petroleum jelly and liquid paraffin in a 1.2:2.8:1 ratio. These formulated mixtures were then tested using the above methodology and were repeated after 2, 4, 6 and 8 hours to give PE over time.

Results

The human-derived compounds tested against *Anopheles gambiae* s.s. gave dose-dependent repellency, with the maximum repellency observed for compounds at 10%. 100% repellency was recorded only for geranylacetone at 10%.

DEET gave better repellency than the single compounds giving 100% repellency at 1% and 10% (Tables 5-7). However, the greatest repellency against this species was given by mixture 3, which achieved 100% repellency at concentrations of 1% and 10%.

At lower concentrations than these, good repellency was also observed and at 0.1% concentration 87% repellency was recorded in comparison with DEET which gave only 83% repellency. At a lower concentration (0.01%) mixture 3 gave 80% repellency compared with DEET which gave only 20% repellency at this concentration (Tables 8-10). All formulated mixtures gave 100% repellency at the start of the experiments (i.e. time zero). Around 90% repellency was achieved after 2 hours with mixture 1 and this decreased over time to 12% after 8 hours (Tables 11-13). Greater repellency was observed for mixture 3 with 98% repellency recorded after 2 hours. Repellency then decreased to 64% after 4 hours and to 35% after 8 hours. DEET maintained 100% effectiveness up to 6 hours and 94% after 8 hours.

The human-derived compounds tested against *Culex quinquefasciatus* gave dose-dependent repellency, with the highest repellency for each compound observed at 10%. Geranylacetone and DEET gave 100% repellency but only at a concentration of 10% (Tables 14-16).

Mixture 1 and 3 gave 100% repellency at a concentration of 10%. At lower concentrations, mixture 1 gave greater repellency than mixture 3 with 84% and 77% repellency achieved respectively at a concentration of 1%. Both formulated mixtures gave 100% repellency at the start of the experiment, and this decreased slightly to 89% for mixture 1 and to 99% for mixture 3 after 2 hours (Tables 17 and 18).

After 8 hours, the repellency given by mixture 1 had decreased to 20%. However, for mixture 3, repellency was maintained at a greater level, decreasing only to 80% after 4 hours, 60% after 6 hours and 45% after 8 hours. DEET gave 100% repellency up until 6 hours and this decreased to 93% after 8 hours (Tables 19-21).

CONCLUSIONS

The most effective treatment against *Anopheles gambiae* over 3 minutes was mixture 3 and this was better than DEET at equivalent concentrations. For *Culex quinquefasciatus*, the most effective treatment was decanal alone at 1%, although this was not better than DEET. The best treatment comprising human-derived compounds was mixture 3 for both species.

TABLE 1

Insect and Tick targets.

| INSECT | DISEASES VECTORED | COUNTRY | IRRITATION TO HOST |
|---|---|---|---|
| Mosquitoes | | | |
| *Culex pipiens* complex | West Nile Virus Japanese Encephalitis Filariasis | USA Asia South America, Africa | Yes |
| *Aedes aegypti* | Dengue fever Yellow fever | South America and Africa | Yes |
| *Anopheles stephensi* | Malaria | Asia | Yes |
| *Anopheles gambiae* complex | Malaria | Africa | Yes |
| Midges | | | |
| *Culicoides impunctatus* | None | Scotland, UK | Yes |
| *Culicoides molestus* | None | Australia | Yes |
| Ticks | | | |
| Ixodid species (*Borrelia*) | Borreliosis and Lyme disease | EU and USA | No |
| Sandflies | | | |
| *Lutzomyia* species | Leishmaniasis (visceral, mucosal, cuticular) | EU, Portugal South America | Yes Yes |
| *Phlebotomine* species | Leishmaniasis | Africa | Yes |
| Midges | | | |
| Other *Culicoides* midges | Bluetongue African Horse Sickness | EU and Africa | Yes |
| Ticks | | | |
| Ixodid ticks | Tick-borne encephalitis Tick-borne fever | North America Africa | No |

TABLE 2

Names and retention indices for 24 EAG-active chemicals with loadings from CVA.

| Compound no | Retention Index | Compound name | Latent vectors (loadings) |
|---|---|---|---|
| 1 | 776 | Hexanal | 0.00044 |
| 2 | 932 | Benzaldehyde | 0.00133 |
| 3 | 965 | 6-Methyl-5-hepten-2-one | −0.00427 |
| 4 | 980 | Octanal | 0.00062 |
| 5 | 988 | 1,4-Dichlorobenzene | 0.00126 |
| 6 | 1010 | 2-Ethylhexanol | 0.00117 |
| 7 | 1022 | Limonene | −0.0005 |
| 8 | 1030 | Unknown 7 | 0.00016 |
| 9 | 1057 | Dihydromyrcenol | −0.00082 |
| 10 | 1080 | Nonanal | −0.00047 |
| 11 | 1083 | Linalool | 0.00047 |
| 12 | 1100 | Undecane | 0.0001 |
| 13 | 1135 | (E)-2-nonenal | 0.00011 |
| 14 | 1151 | Octanoic acid | 0.00056 |
| 15 | 1160 | Menthol | 0.00097 |
| 16 | 1160 | Naphthalene | −0.00102 |
| 17 | 1184 | Decanal | −0.00245 |
| 18 | 1256 | Indole | −0.00233 |
| 19 | 1384 | Dodecanal | −0.00122 |
| 20 | 1430 | Geranylacetone | 0.00042 |
| 21 | 1480 | α-isomethylionone | 0.00037 |
| 22 | 1500 | Pentadecane | −0.00067 |
| 23 | 1600 | Hexadecane | −0.00024 |
| 24 | 1681 | Heptadecene | 0.00115 |

TABLE 3a

Ratios of compounds based on mean amounts of chemicals from "attractive" volunteers and "unattractive" volunteers.

| Compound | Attractive | Unattractive |
| --- | --- | --- |
| Benzaldehyde | 1 | 1 |
| 6-MHO | 2.020595 | 1.55218 |
| Octanal | 0.541551 | 0.529534 |
| Nonanal | 6.510643 | 2.906716 |
| Naphthalene | 0.875217 | 0.979441 |
| Decanal | 1.821094 | 1.468768 |
| Geranylacetone | 5.130115 | 1.108576 |

TABLE 3b

Ratios of 6-methyl-5-hepten-2-one to geranylacetone
The table shows the ratio in one unattractive volunteer and the ratios for the mean absolute amounts of the attractive and unattractive group of volunteers.

| | Standard unattractive person | | Attractive group Mean | | Unattractive group Mean | |
| --- | --- | --- | --- | --- | --- | --- |
| | Absolute amount | Ratio | absolute amount | Ratio | absolute amount | Ratio |
| 6-methyl-5-hepten-2-one | 350.0 | 1.8 | 49.73 | 0.4 | 320.08 | 1.4 |
| Geranylacetone | 200 | 1 | 126.26 | 1 | 228.6 | 1 |

TABLE 4

Mixtures of EAG-active human-derived compounds tested on *C. impunctatus* in the field.

| | |
| --- | --- |
| Mixture 1 | 1% 6-methyl-hepten-2-one, 0.01% octanal (in ethanol) |
| Mixture 2 | 1% 6-methyl-hepten-2-one, 0.01% octanal, 0.02% geranylacetone (in ethanol) |
| Mixture 3 | 1% 6-methyl-hepten-2-one, 1% geranylacetone, 0.01% octanal (in ethanol) |
| Mixture 4 | 1% 6-methyl-hepten-2-one, 0.0001% geranylacetone, 0.01% octanal (in ethanol) |
| Mixture 5 | 1% 6-methyl-hepten-2-one, 1% geranylacetone (in ethanol) |
| Mixture 6 | 1% geranylacetone, 0.01% octanal (in ethanol) |

TABLE 5

Dose-response repellency of geranylacetonedecanal tested against *An. gambiae*

| | % Conc. | | | | |
| --- | --- | --- | --- | --- | --- |
| | 0.001 | 0.01 | 0.1 | 1 | 10 |
| Mean % P.E ± S.E | 7.25 ± 9.5 | 11.17 ± 12.9 | 30.13 ± 11 | 76.97 ± 5.9 | 100 ± 0 |

TABLE 6

Dose-response repellency of 6-methyl-5-hepten-2-one tested against *An. gambiae*

| | % Conc. | | | | | |
| --- | --- | --- | --- | --- | --- | --- |
| | 0.0001 | 0.001 | 0.01 | 0.1 | 1 | 10 |
| Mean % P.E ± S.E | 0.85 ± 3.9 | 1.57 ± 11.2 | 19.2 ± 5.5 | 34.07 ± 6.6 | 35.73 ± 8.7 | 74.75 ± 6.1 |

TABLE 7

Dose-response repellency of DEET tested against *An. gambiae*

| | % Conc. | | | | |
| --- | --- | --- | --- | --- | --- |
| | 0.001 | 0.01 | 0.1 | 1 | 10 |
| Mean % P.E ± S.E | 6.23 ± 1.7 | 20.65 ± 6.4 | 83.78 ± 3.9 | 100 ± 0 | 100 ± 0 |

TABLE 8

Dose-response repellency of Mixture 1: 1:1:1:1:1 of 6MHO:Octanal:Nonanal:Decanal:Geranylacetone tested against *An. gambiae*

| | % Conc. | | | | |
| --- | --- | --- | --- | --- | --- |
| | 0.001 | 0.01 | 0.1 | 1 | 10 |
| Mean % P.E ± SE | 9.2 ± 1.8 | 16.93 ± 3.5 | 44.58 ± 1.1 | 94.1 ± 1.1 | 100 ± 0 |

TABLE 9

Dose-response repellency of Mixture 2: 1:3:1:0.5:0.5 of 6MHO:Octanal:Nonanal:Decanal:Geranylacetone tested against *An. gambiae*

| | % Conc. | | | | |
| --- | --- | --- | --- | --- | --- |
| | 0.001 | 0.01 | 0.1 | 1 | 10 |
| Mean % P.E ± SE | −3.47 ± 6.4 | 16.50 ± 5.1 | 26.93 ± 3.7 | 59.48 ± 3.1 | 100.00 ± 0 |

TABLE 10

Dose-response repellency of Mixture 3: 1:1 of 6MHO:Geranylacetone tested against *An. gambiae*

| | % Conc. | | | | | |
|---|---|---|---|---|---|---|
| | 0.0001 | 0.001 | 0.01 | 0.1 | 1 | 10 |
| Mean % P.E ± SE | 9.4 ± 2.3 | 24.38 ± 5.1 | 79.42 ± 3.7 | 87.08 ± 3.1 | 100 ± 0 | 100 ± 0 |

TABLE 11

Dose-response repellency of formulated Mixture 1: 1:1:1:1:1 of 6MHO:Octanal:Nonanal:Decanal:Geranylacetone (10% concentration) tested against *An. gambiae* over 8 hours.

| | Duration (hrs) | | | | |
|---|---|---|---|---|---|
| | 0 H | 2 H | 4 H | 6 H | 8 H |
| Mean % P.E ± S.E | 100 ± 0 | 89.41 ± 3.67 | 54.87 ± 4.49 | 32.11 ± 5.59 | 12.50 ± 2.1 |

TABLE 12

Dose-response repellency of formulated Mixture 3: 1:1 of 6MHO:Geranylacetone (10% concentration) tested against *An. gambiae* over 8 hours.

| | Duration (hrs) | | | | |
|---|---|---|---|---|---|
| | 0 H | 2 H | 4 H | 6 H | 8 H |
| Mean % P.E ± S.E | 100 ± 0 | 98.48 ± 1.51 | 64.26 ± 6.15 | 38.82 ± 4.31 | 30.83 ± 6.96 |

TABLE 13

Dose-response repellency of formulated DEET (10% concentration) tested against *An. gambiae* over 8 hours.

| | Duration (hrs) | | | | |
|---|---|---|---|---|---|
| | 0 H | 2 H | 4 H | 6 H | 8 H |
| Mean % P.E ± S.E | 100 ± 0 | 100 ± 0 | 100 ± 0 | 100 ± 0 | 94.35 ± 1.02 |

TABLE 14

Dose-response repellency of geranylacetone tested against *Culex quinquefasciatus*

| | % Conc. | | | | | |
|---|---|---|---|---|---|---|
| | 0.0001 | 0.001 | 0.01 | 0.1 | 1 | 10 |
| Mean % P.E ± S.E | 4.8 ± 2.4 | 10 ± 1.6 | 23.7 ± 4.5 | 33.2 ± 4.5 | 84.1 ± 4.2 | 100 ± 0 |

TABLE 15

Dose-response repellency of 6-methyl-5-hetpen-2-one tested against *Culex quinquefasciatus*

| | % Conc. | | | | | |
|---|---|---|---|---|---|---|
| | 0.0001 | 0.001 | 0.01 | 0.1 | 1 | 10 |
| Mean % P.E ± S.E | 8.0 ± 1.8 | 12.7 ± 2.1 | 21.8 ± 4.9 | 30.1 ± 4.1 | 49.7 ± 2.9 | 100.0 ± 0 |

TABLE 16

Dose-response repellency of DEET tested against *Culex quinquefasciatus*

| | % Conc. | | | | |
|---|---|---|---|---|---|
| | 0.001 | 0.01 | 0.1 | 1 | 10 |
| Mean % P.E ± S.E | 7.6 ± 1.8 | 12.0 ± 1.7 | 76.9 ± 5.4 | 98.2 ± 1.1 | 100 ± 0 |

TABLE 17

Dose-response repellency of Mixture 1: 1:1:1:1:1 of 6MHO:Octanal:Nonanal:Decanal:Geranylacetone tested against *Culex quinquefasciatus*

| | Conc. | | | | |
|---|---|---|---|---|---|
| | 0.001 | 0.01 | 0.1 | 1 | 10 |
| Mean % P.E ± S.E | 9.61 ± 3.53 | 20.82 ± 4.86 | 33.46 ± 3.76 | 84.06 ± 6.94 | 100 ± 0 |

TABLE 18

Dose-response repellency of Mixture 3: 1:1 of 6MHO:Geranylacetone (at 10% concentration) tested against *Culex quinquefasciatus*

| | Conc. | | | | |
|---|---|---|---|---|---|
| | 0.001 | 0.01 | 0.1 | 1 | 10 |
| Mean % P.E ± S.E | 11.27 ± 1.86 | 20.83 ± 2.26 | 55.64 ± 5.81 | 77.00 ± 4.53 | 100 ± 0 |

TABLE 19

Dose-response repellency of formulated Mixture 1: 1:1:1:1:1 of 6MHO:Octanal:Nonanal:Decanal:Geranylacetone (at 10% concentration) tested against *Culex quinquefasciatus* over 8 hours.

| | Duration (hrs) | | | | |
|---|---|---|---|---|---|
| | 0 H | 2 H | 4 H | 6 H | 8 H |
| Mean % P.E ± S.E | 100 ± 0 | 89.03 ± 4.2 | 56.17 ± 4.37 | 28.46 ± 5.15 | 19.83 ± 3.16 |

TABLE 20

Dose-response repellency of formulated Mixture 3: 1:1 of 6MHO:Geranylacetone (at 10% concentration) tested against *Culex quinquefasciatus* over 8 hours.

| | Duration (hrs) | | | | |
|---|---|---|---|---|---|
| | 0 H | 2 H | 4 H | 6 H | 8 H |
| Mean % P.E ± S.E | 100 ± 0 | 98.57 ± 1.43 | 79.97 ± 1.7 | 60.91 ± 3.1 | 45.79 ± 4.13 |

TABLE 21

Dose-response repellency of formulated DEET (at 10% concentration) tested against *Culex quinquefasciatus* over 8 hours.

| | Duration (hrs) | | | | |
|---|---|---|---|---|---|
| | 0 H | 2 H | 4 H | 6 H | 8 H |
| Mean % P.E ± S.E | 100 ± 0 | 100 ± 0 | 100 ± 0 | 100 ± 0 | 93.33 ± 4.08 |

REFERENCE LIST

1. Brouwer, R. (1960). "Variations in human body odour as a cause of individual differences of attraction for malaria mosquitoes." *V. Trop. Geoqr. Med.* 12: 186-192.
2. Khan, A. A. and H. I. Maibach (1966). "Quantitation of Effect of Several Stimuli on Landing and Probing by Aedes Aegypti." *Journal of Economic Entomology* 59(4): 902-&.
3. Mayer, M. S. and J. D. James (1969). "Attraction of *Aedes Aegypti* (L)—Responses to Human Arms Carbon Dioxide and Air Currents in a New Type of Olfactometer." *Bulletin of Entomological Research* 58: 629-&.
4. Burkot, T. R. (1988). "Non-Random Host Selection by Anopheline Mosquitos." *Parasitology Today* 4(6): 156-162.
5. Schreck, C. E., D. L. Kline, et al. (1990). "Mosquito Attraction to Substances from the Skin of Different Humans." *Journal of the American Mosquito Control Association* 6(3): 406-410.
6. Brady, J., C. Costantini, et al. (1997). "The role of body odours in the relative attractiveness of different men to malarial vectors in Burkina Faso." *Annals of Tropical Medicine and Parasitology* 91: S121-S122.
7. Costantini, C. S., N. Gibson, G. Coluzzi, M. (1997). "The role of body odours in the relative attractiveness of different men to malarial vectors in Burkino Faso." *Annals of Tropical Medicine and Parasitology* 91(1): s121-s122.
8. Lindsay, S. W., J. H. Adiamah, et al. (1993). "Variation in Attractiveness of Human-Subjects to Malaria Mosquitos (Diptera, Culicidae) in the Gambia." *Journal of Medical Entomology* 30(2): 368-373.
9. Qie Y T, Smallegange R. C., Hoppe S. van Loon J. J., Bakker E. J., Takken W. (2004) Behavioural and electrophysiological responses of the malaria mosquito *Anopheles gambiae* Giles sensu stricto (Diptera: Culicidae) to human skin emanations. Med and Vet Entomol. Dec. 18 (4): 429-38
10. Acree, F., R. B. Turner, et al. (1968). "L-Lactic Acid—a Mosquito Attractant Isolated from Humans." *Science* 161 (3848): 1346-&.
11. Smith, C. N., N. Smith, et al. (1970). "L-Lactic Acid as a Factor in Attraction of *Aedes-Aegypti* (Diptera-Culicidae) to Human Hosts." *Annals of the Entomological Society of America* 63(3): 760-&.
12. Steib, B. M., M. Geier, et al. (2001). "The effect of lactic acid on odour-related host preference of yellow fever mosquitoes." *Chemical Senses* 26(5): 523-528.
13. Bernier, U., Kline, D L, Schreck, C E, Yost, R A, Barnard, D R. (2002). "Chemical analysis of human skin emanations: comparison of volatiles from humans that differ in attraction of *Aedes aegypti* (Diptera: Culicidae)." *J Am Mosq Control Assoc.* 18(3): 186-95.
14. Takken, W. and B. G. J. Knols (1999). "Odor-mediated behavior of Afrotropical malaria mosquitoes." *Annual Review of Entomology* 44: 131-157.
15. Costantini, C., Sagnon, N. F., della Torre, A., Diallo, M., Brady, J., et al. (1998) Odour-mediated host preferences of West African mosquitoes, with particular reference to malaria vectors. *American Journal of Tropical Medicine and Hygiene,* 58, 56-63.
16. Bernier, U. R., D. L. Kline, et al. (2000). "Analysis of human skin emanations by gas chromatography/mass spectrometry. 2. Identification of volatile compounds that are candidate attractants for the yellow fever mosquito (*Aedes aegypti*)." *Analytical Chemistry* 72(4): 747-756.
17. Geier, M. and J. Boeckh (1999). "A new Y-tube olfactometer for mosquitoes to measure the attractiveness of host odours." *Entomologia Experimentalis Et Applicata* 92(1): 9-19.
18. WHO (1996) Report of the WHO Informal Consultation on the evaluation and testing of insecticides, WHO, Geneva, Ref: CTD/WHOPES/IC/96.1 http://whqlibdoc.who.int/hq/1996/CTD_WHOPES_IC_96.1.pdf
19. S. Carpenter, K. Eyres, I. McEndrick, L. Smith, J. Turner, W. Mordue and A. J. Mordue (Luntz) (2005) Repellent efficiency of BayRepel against *Culicoides impunctatus* (Diptera: Ceratopogonidae) Parasitology Research 95 (6): 427-429.

The invention claimed is:

1. A method of inhibiting the activity of a haematophagous arthropod against a subject, which method comprises applying a composition to the subject, which composition comprises geranylacetone as an active ingredient plus a further active ingredient which is 6-methyl-5-hepten-2-one,
    wherein the 6-methyl-5-hepten-2-one and geranylacetone are present in a weight ratio of about 1:1, and
    wherein the geranylacetone and the 6-methyl-5-heptene-2-one are both present in proportions in the range: 0.001 -0.1% by weight.

2. A method as claimed in claim 1 wherein the subject is a human subject.

3. A method as claimed in claim 1 wherein the haematophagous arthropod is an insect pest in the family Ceratopogonidae or family Culicidae or is a tick.

4. A method as claimed in claim 1 wherein the haematophagous arthropod is selected from the list consisting of: members of the Culex pipiens complex; Aedes aegypti; Anopheles stephensi; Anopheles gambiae complex; Culicoides impunctatus; Culicoides molestus; Lutzomyia species; Phlebotomine species; Midges.

5. The method of claim 2 wherein the composition is applied to the human subject in order to achieve a topical dose of the active ingredients on the human subject of between about 0.0025 µg/cm$^2$ to 100 µg/cm$^2$.

6. A method as claimed in claim 1 wherein the composition is applied as a formulation which is an ointment, solid or solution adapted for topical application, and which further comprises a dermatologically acceptable carrier.

7. A method as claimed in claim 6 which comprises one or more volatile silicon fluids.

8. A method of repelling a haematophagous arthropod from an environment or preventing attraction to an environment, the method comprising applying to the environment a composition which comprises geranylacetone as an active ingredient plus a further active ingredient which is 6-methyl-5-hepten-2-one, wherein the 6-methyl-5-hepten-2-one and geranylacetone are present in a weight ratio of about 1:1 and wherein the geranylacetone and the 6-methyl-5-heptene-2-one are both present in proportions in the range: 0.001-0.1% by weight.

9. A method claim 8 wherein the composition is applied to the environment using a dispenser.

10. The method of claim 9 wherein the dispenser is selected from the list consisting of: a candle, a coil, a slow release dispenser, an oil burner, and an electric diffuser.

11. A method as claimed in claim 9 wherein the dispenser is an electrostatic chemical dispenser.

12. The method of claim 11, wherein the electrostatic chemical dispenser comprises:
a) a conduit that contains liquid to be atomised, which liquid comprises the composition;
b) a spray electrode; and
c) a discharge electrode.

* * * * *